United States Patent [19]

Markofsky et al.

[11] Patent Number: 4,910,343

[45] Date of Patent: Mar. 20, 1990

[54] NITROAMINES

[75] Inventors: Sheldon B. Markofsky, Olney, Md.; Agneta M. Ahlkvist, Helsingborg, Sweden

[73] Assignee: W. R. Grace & Co.-Conn., New York, N.Y.

[21] Appl. No.: 246,610

[22] Filed: Sep. 20, 1988

[51] Int. Cl.$^4$ .................. C07C 87/00; C07C 87/24
[52] U.S. Cl. ................................................ 564/509
[58] Field of Search .................................... 564/509

[56] References Cited

U.S. PATENT DOCUMENTS

| | | | |
|---|---|---|---|
| 2,365,825 | 12/1944 | Kyrides et al. | 564/477 |
| 3,754,041 | 8/1973 | Mitsuyasu et al. | 564/509 |
| 4,353,828 | 10/1982 | Bey et al. | 564/509 |
| 4,698,446 | 10/1987 | Lai et al. | 564/494 |
| 4,792,625 | 12/1988 | Wiener et al. | 564/494 |

FOREIGN PATENT DOCUMENTS 1157637  7/1966  United Kingdom ............... 564/477

OTHER PUBLICATIONS

Merck Index, 10th Ed. 6564.
JACS, 74 3664 (1952).

Primary Examiner—Richard L. Raymond
Assistant Examiner—Raymond Covington
Attorney, Agent, or Firm—Howard J. Troffkin

[57] ABSTRACT

The present invention is directed to certain novel nitroamine compounds, specifically, 1-diethylamino-4-nitropentene-1 and 1-diethylamino-4-nitropentane. The present invention is further directed to the use of the above-mentioned compounds in the formation of novoldiamine.

4 Claims, 4 Drawing Sheets

NITROAMINES

BACKGROUND OF THE INVENTION

The present invention is directed to certain novel nitroamine compounds and to their utilization in the formation of novoldiamine, compound required to form the antimalarial drug, chloroquine.

Novoldiamine is presently prepared by a complex synthesis. The compound is prepared commercially from 2-diethylaminoethanol and ethyl acetoacetate. The alcohol is reacted with thionyl chloride to form 2-chlorotriethylamine (A) while the acetoacetate is reacted with sodium ethoxide to provide the sodium derivative of ethyl acetoacetate (B). The initially formed compounds A and B are then condensed to yield an intermediate ester which must be hydrolyzed and then decarboxylated to provide 5-diethylamino-2-pentanone (C). This product (C) is hydrogenated in the presence of ammonia to produce the subject novoldiamine product. Other modes of preparation are known (See U.S. Pat. No. 2,365,825), but are not practiced due to the complexity of the synthesis.

It is an object of the present invention to provide certain novel nitroamine compounds.

It is a further object of the present invention to provide a simple and economical method of producing novoldiamine by utilizing certain novel compounds fully described hereinbelow.

SUMMARY OF THE INVENTION

The present invention is directed to certain novel nitroamine compounds. Specifically, the compounds are an enamine compound, 1-diethylamino-4-nitropentene-1 and its partially reduced counterpart, 1-diethylamino-4-nitropentane. These compounds have been found to provide and permit a new synthetic route to the formation of novoldiamine and ultimately, the antimalaria drug, chloroquine.

DETAILED DESCRIPTION

The present invention is directed to a new and novel method of forming novoldiamine and, in addition, to new nitrocompounds, 1-diethylamino-4-nitropentene-1 (I) and 1-diethylamino-4-nitropentane (II).

The compound, 1-diethylamino-4-nitropentene-1, is an enamine having the structural formula:

$$CH_3CHCH_2CH=CHN(CH_2CH_3)_2 \quad (I)$$

with $NO_2$ on the first carbon.

This compound has been formed from readily available starting reagents, nitroethane, acrolein and diethylamine.

The nitroethane and acrolein are initially reacted together to form 4-nitrovaleraldehyde by a Michael-type reaction in the same manner as disclosed in Addition Reactions of Nitroalkanes and Acrolein and Methyl Vinyl Ketone, J.A.C.S. 74 3664 (1952) which teaching is incorporated herein by reference.

The enamine (I) is then formed by contacting diethylamine with the 4-nitrovaleraldehyde in a common solvent at low temperatures of from about 10° to 100° C., preferably from about 10° to 50° C. The reaction is somewhat exothermic and, therefore, a means for controlling temperature may be needed. The reaction should, preferably, be carried out in the presence of a known drying agent as the water by-product tends to hydrolyze the enamine product back to the starting materials and thus slows the reaction or reduces the yield. Typical drying agents which can be used include molecular sieves, as well as anhydrous salts of magnesium sulfate, sodium sulfate, calcium chloride, calcium sulfate and the like.

The reaction is carried out in high yields in a time period of from about 10 to 240 minutes (normally from about 20 to 120 minutes) depending on reaction conditions used.

The nitrovaleraldehyde and diethylamine reactants described above should be contacted in a liquid medium which is inert to the reaction and is capable of dissolving the reactants. Examples of such solvents include lower alkyl ($C_1$–$C_5$) alcohols, such as methanol, ethanol, isopropanol and the like; ethers such as dialkyl (preferably $C_1$–$C_3$) ethers and cyclic ethers, such as tetrahydrofuran and the like; aromatic compounds, such as benzene, toluene and the like; esters, such as ethyl acetate and the like; sulfoxides, such as dimethylsulfoxide and the like; and halocarbons such as methylene chloride and the like. The solvent must be inert to the reaction as can be determined by conventional experimentation, capable of dissolving the majority of the nitroaldehyde and dialkylamine reactants under reaction conditions and be capable of remaining a liquid solution under such conditions.

The product of the above described synthesis has been determined to be a novel enamine compound of the formula (I) given above. The resulting enamine, 1-diethylamino-4-nitropentene-1, is a necessary compound for the formation of novoldiamine by a synthesis described hereinbelow.

Figure 1:
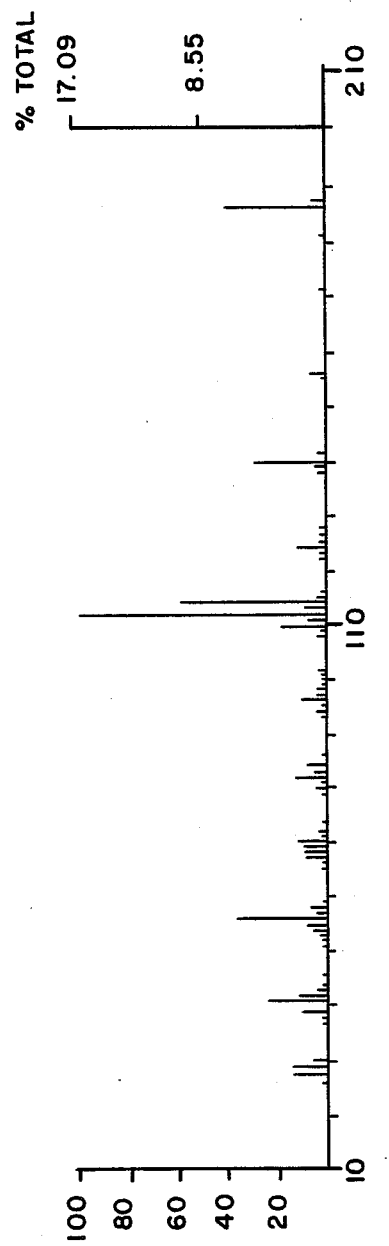
Figure 2:
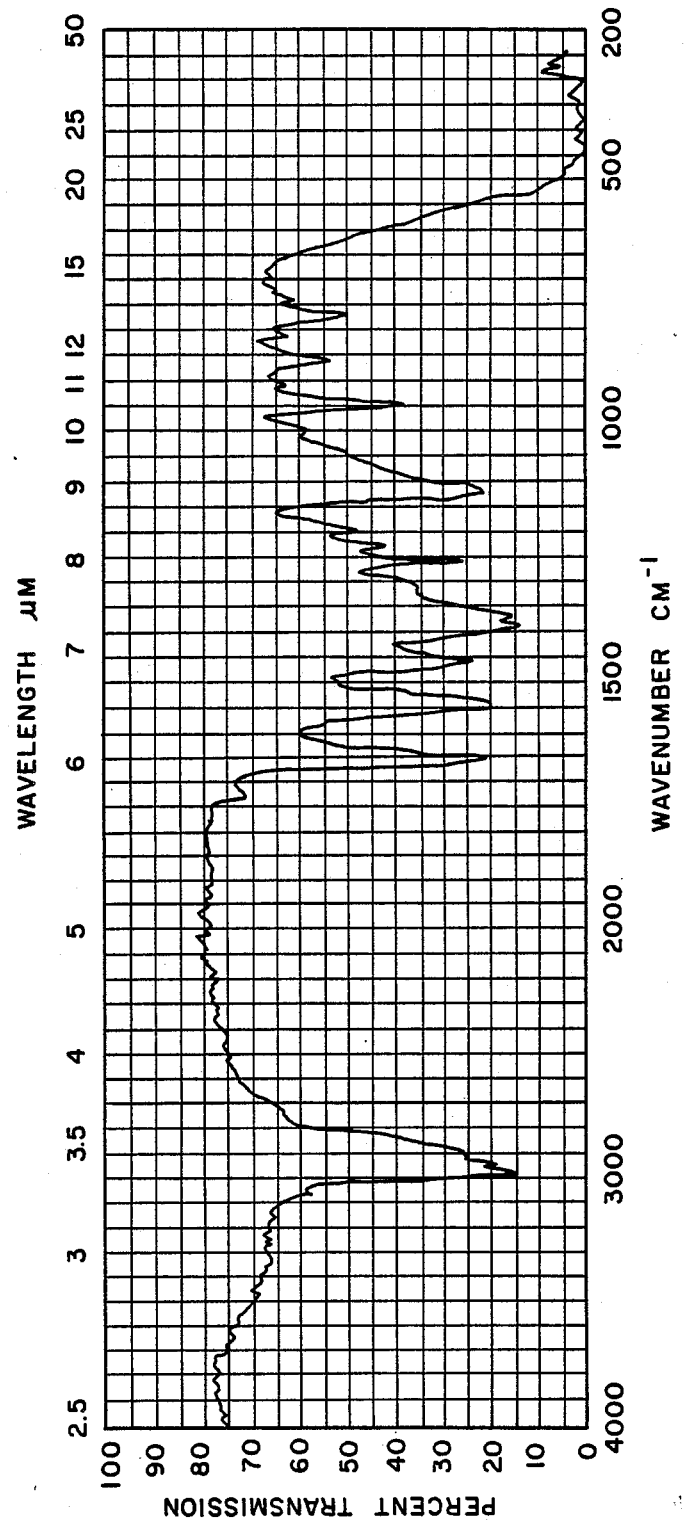

The enamine (I) is a liquid having a mass spectral graph as shown in FIG. 1 and an infared spectra (in $CH_2Cl_2$) as shown in FIG. 2. The compound is further identified by formation of its pentane derivative, as described below.

1-Diethylamino-4-nitropentane (II) can be formed by reductive hydrogenation of compound (I) which is selective to the enamine group while retaining the nitro group. Such reduction can be carried out by utilizing mild hydrogenation conditions, that is, either the reaction conditions of temperature and pressure are sufficiently mild and/or the hydrogenation catalyst is sufficiently mild under the reaction conditions or both to permit reduction of the enamine group while retaining the nitro group. The temperature range which is found suitable is from about 10° to 200° C. with from 10° to 100° C. being preferred. The hydrogen contained in the reaction zone should cause a pressure of from about 100 to 1000 psi. The reaction must be carried out in the presence of at least one known hydrogenation catalyst material. Examples of such catalysts include Group VIII metal catalysts such as supported platinum, palladium, cobalt, nickel, rhodium and the like. The support can be carbon, silicon, clays and the like. In addition, Raney nickel or Raney cobalt can be used (these catalysts are Ni-Al or Co-Al alloys which have had the surface aluminum removed by alkali treatment). Soluble Group VIII metal catalyst material, such as rhodium carbonyls and the like can also be used. The preferred catalysts are formed from rhodium, cobalt and platinum. Rhodium carbonyls provide very high yield of (II). The hydrogenation catalysts useful herein are conventional agents known to provide catalytic effect for reductive hydrogenation.

The reduction can be carried out by having the enamine I in an aprotic solvent such as ethers and the like. The reduction is carried out in conventional manners with the proviso that the conditions are sufficiently mild so that only the enamine group is reduced while substantially retaining the nitro group. The solution contains the hydrogenation catalyst either as a homogeneous (i.e., $Rh_6(CO)_{16}$) or as a heterogeneous (i.e., Pd/C) material therein.

Figure 3:
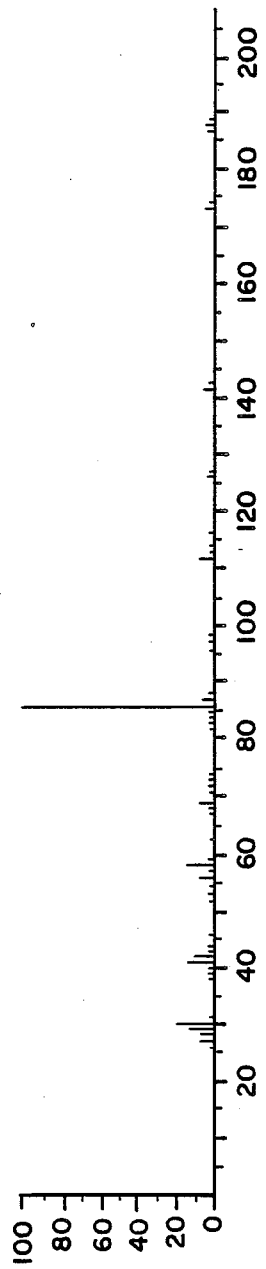
Figure 4:
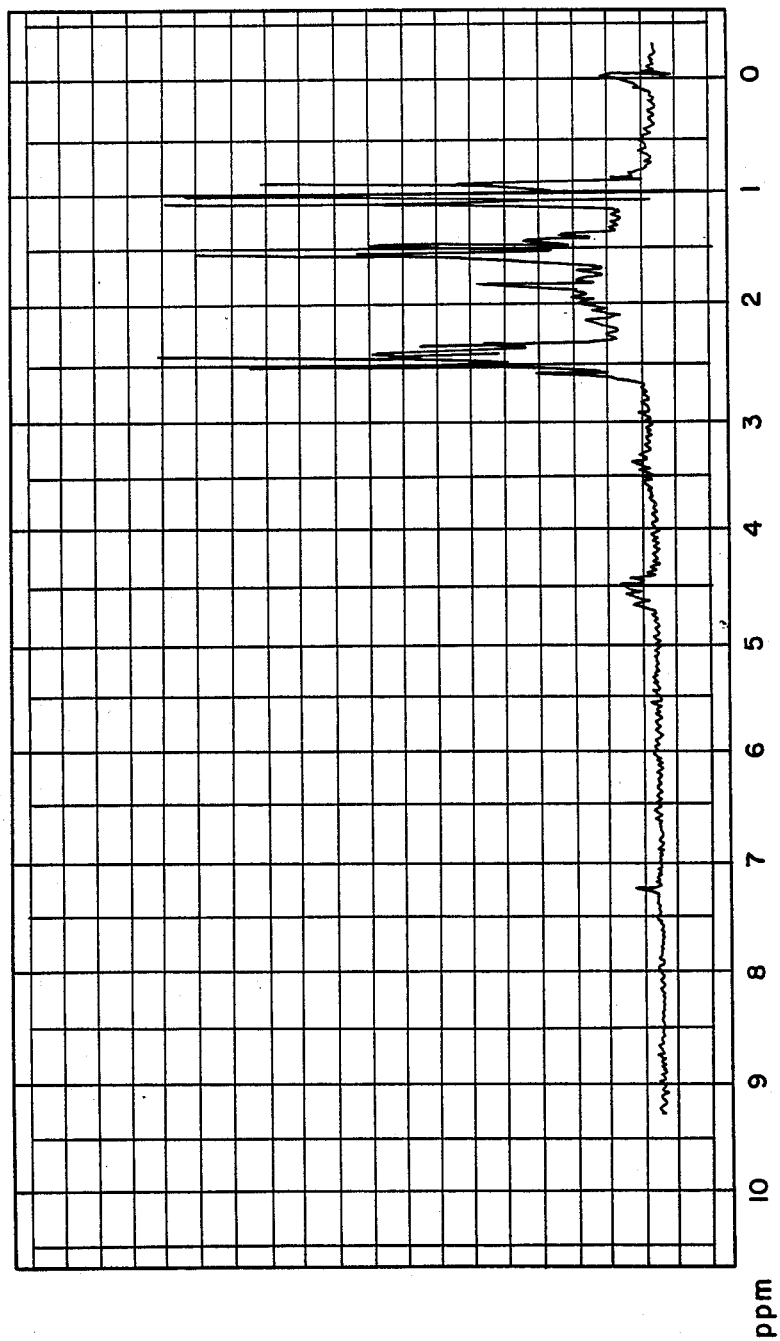

The compound II is a liquid having a boiling point of 76° C. at 0.3 mm pressure. The product has a mass spectral graph as shown in FIG. 3 and an NMR (Nuclear Magnetic Resonance) spectra (a 390 Spectrometer) as shown in Figure 4.

The subject compounds I and II as described above provide a means of establishing a new synthetic route to provide novoldiamine. The new route utilizes readily available and inexpensive starting materials, and the process steps are few and simple to accomplish. The presently described process provides a new, simple and economically attractive method to produce novoldiamine.

The synthesis requires the initial formation of the nitro enamine compound (I) described hereinabove. This is accomplished by reacting nitroethane and acrolein to form 4-nitrovaleraldehyde which is then reacted with diethylamine to yield the nitro enamine (I). The enamine (I) is then reduced to compound II described above by selective hydrogenation of the enamine group and then further subjected to stringent reductive hydrogenation (high temperature, high pressure and/or highly active catalyst) to convert the nitro group to an amino group. The second phase of the reductive hydrogenation can be conducted in a continuous mode with respect to the first phase reduction by merely altering the reaction conditions and/or by introducing a more active catalyst material. For example, the first phase reduction can be conducted at temperatures of from about 10° to 200° C., at low $H_2$ pressure of from about 100 to 1000 psi using a conventional hydrogenation catalyst known to have low to moderate activity. For example, 400 psi $CO/H_2$ at a 1:1 ratio, 100° C. and $Rh_6(CO)_{16}$ in tetrahydrofuran solution.) The second phase reduction can be conducted at temperatures of from 50°–500° C., at $H_2$ pressure of from 250 to 2500 psi and with the aid of highly active hydrogenation catalyst conditions. (For example, 400 psi, 150° C. and Raney Ni in methanol.) The exact combination of temperature, $H_2$ pressure and particular catalyst which will perform a first phase selective reduction and those which will be suitable to aid in performing the second phase reduction (reduction of nitro to amine) can be readily determined by the artisan having the guidance of the present description. Even though the temperature and pressure conditions may be similar in both phases, the combination of reaction conditions must be different to first permit reduction of the enamine e and then reduction of the nitro group. Simultaneous reduction of both the enamine and nitro groups leads to a high degree of by-product formation. The product of the second phase reduction, that is, the reduction of the nitro group to an amino group produces the desired novoldiamine.

The overall synthesis is shown below:

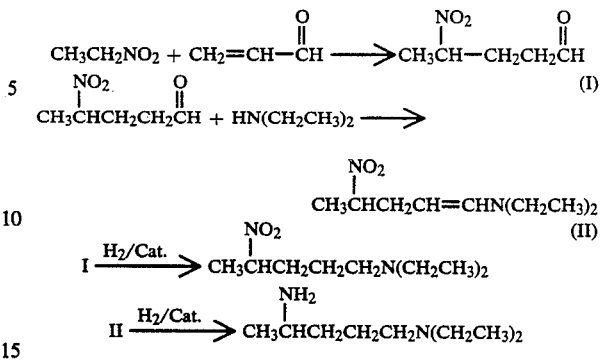

The following examples are give for illustrative purposes only and are not meant to be a limitation on the invention as defined by the claim appended hereto. All parts and percentages are by weight unless otherwise indicated.

EXAMPLE 1

3.3 parts of diethylamine was mixed with 20 parts of tetrahydrofuran (THF) in a glass round bottom flask. 5 parts of 4-nitrovaleraldehyde in 20 parts THF was added dropwise over a 10 minute period at room temperature. The low temperature was maintained by immersing the reaction flask in a water bath. The reaction was complete in a short period. A sample of the solution was analyzed by gas chromotography/mass spectrometry (FIG. 1) and established the product formed to be the enamine, 1-diethylamine-4-nitropentene-1. The product solution was stripped of THF and taken up in methylene chloride. The infrared spectra of this solution (FIG. 2) further confirmed the nitro enamine by absorption bands at 1650 $cm^{-1}$ for the enamine group and 1540–1550 $cm^{31\ 1}$ and 1380 for the nitro group.

EXAMPLE 2

The solution of Example 1 above was placed in a stainless steel sealed reactor together with 0.5 part of palladium on carbon catalyst containing 5 percent palladium. The reactor was charged with hydrogen to 450 psi and remained sealed for 16 hours while maintaining the temperature at 25° C. This mild hydrogenation produced the saturated product, 1-diethylamino-4-nitropentane in 80% yields as shown by gas chromographic analysis. The isolated product was analyzed by mass spectrometry (EM-390 spectrometer) as shown in FIG. 3 and by $^1$H-NMR as shown in FIG. 4.

EXAMPLE 3

A solution prepared according to Example 2 above was subjected to further and more severe hydrogenation by introducing 3 parts water to the solution, charging the reaction vessel with hydrogen to 450 psi pressure and then raising and maintaining an elevated temperature of 70° C. for 4 hours. The product, 4-amino-1-diethylaminopentane was obtained in 80% yield (based on the nitropentane) as determined by gas chromatography using an internal standard.

EXAMPLE 4

The enamine was prepared according to the procedure of Examples 1 above except that the solvent was ethyl acetate. Selective hydrogenation of the enamine was carried out according to Example 2 except that the conditions were 60 psi H₂ pressure and room temperature. The enamine was produced in 80% yield as determined by gas chromatography.

EXAMPLE 5

The solution of Example 4 was neutralized with acetic acid and 5 parts ethanol was added. The hydrogenation was again commenced by charging the vessel with 60 psi H₂ pressure and then elevating the temperature to 70° C. and maintaining these conditons for 6 hours. The yield of 4-amino-1-diethylaminopentane(-based on the nitropentane) was 50%.

EXAMPLE 6

The enamine was prepared by the procedure of Example 1 above using THF as the solvent. The solution was charged into a stainless steel sealed container together with 0.1 part of rhodium carbonyl, Rh₆(CO)₁₆, a known hydrogenation catalyst. Hydrogenation was initially carried out by charging the vessel with 50:50 H₂/CO to 100 psi at room temperature for 6 hours. The partially reduced product was further reduced by carrying out the second phase at 800 psi H₂ pressure and 100° C. for 4 hours. The completed product was obtained in 75% yield.

What is claimed:

1. A compound represented by the formula:

wherein each R represents an ethyl group.

2. A compound represented by the formula:

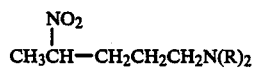

wherein each R separately represents an ethyl group.

3. The compound of claim 1 having a mass spectral analysis of FIG. 1.

4. The compound of claim 2 having a mass spectral analysis of FIG. 3.

* * * * *